US010337757B2

(12) United States Patent
Gutierrez et al.

(10) Patent No.: US 10,337,757 B2
(45) Date of Patent: Jul. 2, 2019

(54) IN-DUCT ACOUSTIC MEASURING APPARATUS AND METHOD

(71) Applicant: The Boeing Company, Chicago, IL (US)

(72) Inventors: Remy M. Gutierrez, Edmonds, WA (US); Bernard J. Sklanka, Maple Valley, WA (US); Ian M. Gunter, Burien, WA (US)

(73) Assignee: THE BOEING COMPANY, Chicago, IL (US)

( * ) Notice: Subject to any disclaimer, the term of this patent is extended or adjusted under 35 U.S.C. 154(b) by 226 days.

(21) Appl. No.: 15/253,787

(22) Filed: Aug. 31, 2016

(65) Prior Publication Data

US 2018/0059070 A1 Mar. 1, 2018

(51) Int. Cl.
| | |
|---|---|
| *H04R 1/08* | (2006.01) |
| *F24F 11/89* | (2018.01) |
| *G01N 29/032* | (2006.01) |
| *G01N 29/036* | (2006.01) |
| *G01N 29/14* | (2006.01) |
| *G01N 29/22* | (2006.01) |
| *F24F 13/02* | (2006.01) |
| *F24F 130/40* | (2018.01) |
| *H04R 29/00* | (2006.01) |

(52) U.S. Cl.
CPC ............ *F24F 11/89* (2018.01); *G01N 29/032* (2013.01); *G01N 29/036* (2013.01); *G01N 29/14* (2013.01); *G01N 29/222* (2013.01); *H04R 1/08* (2013.01); *F24F 13/02* (2013.01); *F24F 2130/40* (2018.01); *G01N 2291/012* (2013.01); *G01N 2291/014* (2013.01); *G01N 2291/015* (2013.01); *H04R 29/006* (2013.01); *H04R 2201/401* (2013.01)

(58) Field of Classification Search
CPC .. F24F 11/89; F24F 13/02; F24F 13/24; F24F 2130/40; G01N 29/032; G01N 29/036; G01N 29/14; G01N 29/222; G01N 2291/012; G01N 2291/014; G01N 2291/015; H04R 1/08; H04R 29/006; H04R 2201/401
USPC ......................................... 73/579, 571, 586
See application file for complete search history.

(56) References Cited

U.S. PATENT DOCUMENTS

| | | |
|---|---|---|
| 3,781,782 A | 12/1973 | Scott et al. |
| 4,144,768 A | 3/1979 | Andersson et al. |
| 4,305,295 A | 12/1981 | Andersson et al. |
| 5,606,622 A | 2/1997 | Christenson |
| 6,201,872 B1 | 3/2001 | Hersh et al. |

(Continued)

*Primary Examiner* — Lisa M Caputo
*Assistant Examiner* — Suman K Nath
(74) *Attorney, Agent, or Firm* — Haynes and Boone, LLP

(57) ABSTRACT

An apparatus and a method for measuring one or more acoustic parameters in a duct are described. The method includes arranging at least one pair of microphones in an array on a microphone support device, disposing the microphone support device including the array of microphones in the duct, generating an acoustic signal in the duct such that the acoustic signal propagates toward the array of microphones, and receiving by the array of microphones, the acoustic signal to provide a microphone output signal. The microphone support device is configured to fit within an inner diameter of the duct.

20 Claims, 10 Drawing Sheets

(56) References Cited

U.S. PATENT DOCUMENTS

| | | | |
|---|---|---|---|
| 2005/0163330 A1* | 7/2005 | Beguet | G01S 3/8036 |
| | | | 381/92 |
| 2005/0207588 A1* | 9/2005 | Biegelsen | H04R 1/403 |
| | | | 381/77 |
| 2007/0220978 A1* | 9/2007 | Su | G01N 29/0681 |
| | | | 73/632 |
| 2009/0290729 A1* | 11/2009 | Zhang | H04R 29/006 |
| | | | 381/122 |
| 2015/0276446 A1* | 10/2015 | Black | G01F 1/66 |
| | | | 73/861.24 |

\* cited by examiner

500
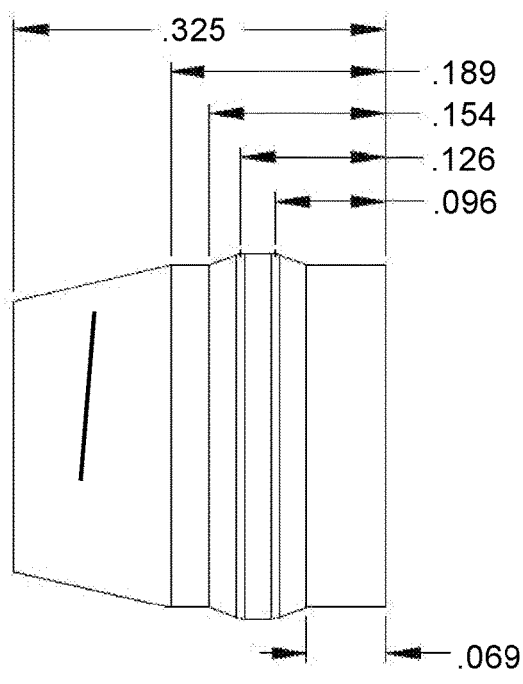
502
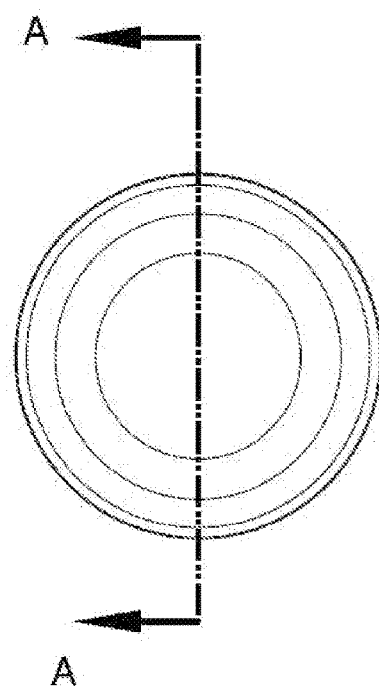
FIG. 5A
FIG. 5B

IN-DUCT ACOUSTIC MEASURING APPARATUS AND METHOD

BACKGROUND

Technical Field

The present application generally relates to measuring acoustic parameters. More particularly, it relates to in-duct acoustic measuring apparatus and method.

Related Art

When environmental control systems, such as heating and/or air conditioning systems are installed, ducting is typically also installed and connected to such systems to direct airflow to desired locations. Whether or not there is airflow in the duct, acoustic waves propagate down the duct from the source of the noise (e.g., air conditioning system) to the other end of the duct (e.g., air vent). It is desirable and often necessary to understand the performance and/or quality of the duct to ensure that certain efficiency is achieved and the integrity of the duct meets design standards (e.g., no leaks or gaps between connections). It is also important to understand the effects of acoustic propagation properties though the ducting. For example, it may be undesirable if an air conditioning system on an aircraft propagates machinery noise from the air conditioning system to the air vent end of the duct near the passengers. However, the frequency range of existing techniques for measuring acoustics in a duct is limited to a relatively narrow frequency range, and when outside of the frequency range, it does not provide accurate information. Therefore, an improved method for measuring acoustic parameters in a duct is needed.

The above information disclosed in this Background section is only for enhancement of understanding of the background of the invention, and therefore, it may contain information that does not form prior art.

SUMMARY

The present disclosure is directed to a method for measuring acoustic parameters in a duct over a wider range of frequencies. An apparatus and a system for obtaining such acoustic measurements are also described.

According to an aspect of an embodiment, a method for measuring one or more acoustic parameters in a duct is described. The method includes arranging at least one pair of microphones in an array on a microphone support device, wherein the microphone support device is configured to fit within an inner diameter of the duct, disposing the microphone support device including the array of microphones in the duct, generating an acoustic signal in the duct such that the acoustic signal propagates toward the array of microphones, and receiving by the array of microphones, the acoustic signal to provide a microphone output signal.

According to another aspect of an embodiment, a method for arranging microphones in a duct for measuring one or more acoustic parameters within the duct is described. The method includes providing a microphone support device, wherein the microphone support device is configured to fit within an inner diameter of the duct, and mounting at least one pair of microphones at predetermined locations along the microphone support device.

According to another aspect of an embodiment, an apparatus configured to measure one or more acoustic parameters in a duct including a microphone support device is described.

According to another aspect of an embodiment, an apparatus is described, which includes a microphone support device configured to fit within an inner diameter of a duct and extend across a cross-section of the duct, and a plurality of microphones arranged in an array on the microphone support device, each of the plurality of microphones being disposed at predetermined locations along the microphone support device.

According to another aspect of an embodiment, a method for phase calibrating a plurality of microphones is described. The method includes determining a phase response for each of the plurality of microphones, and pairing a first microphone of the plurality of microphones with second microphone of the plurality of microphone, wherein a phase response of the first microphone matches a phase response of the second microphone.

BRIEF DESCRIPTION OF THE DRAWINGS

FIGS. 5A-5C illustrate various views of a microphone holder in accordance with an embodiment of the present disclosure

Figure 1:
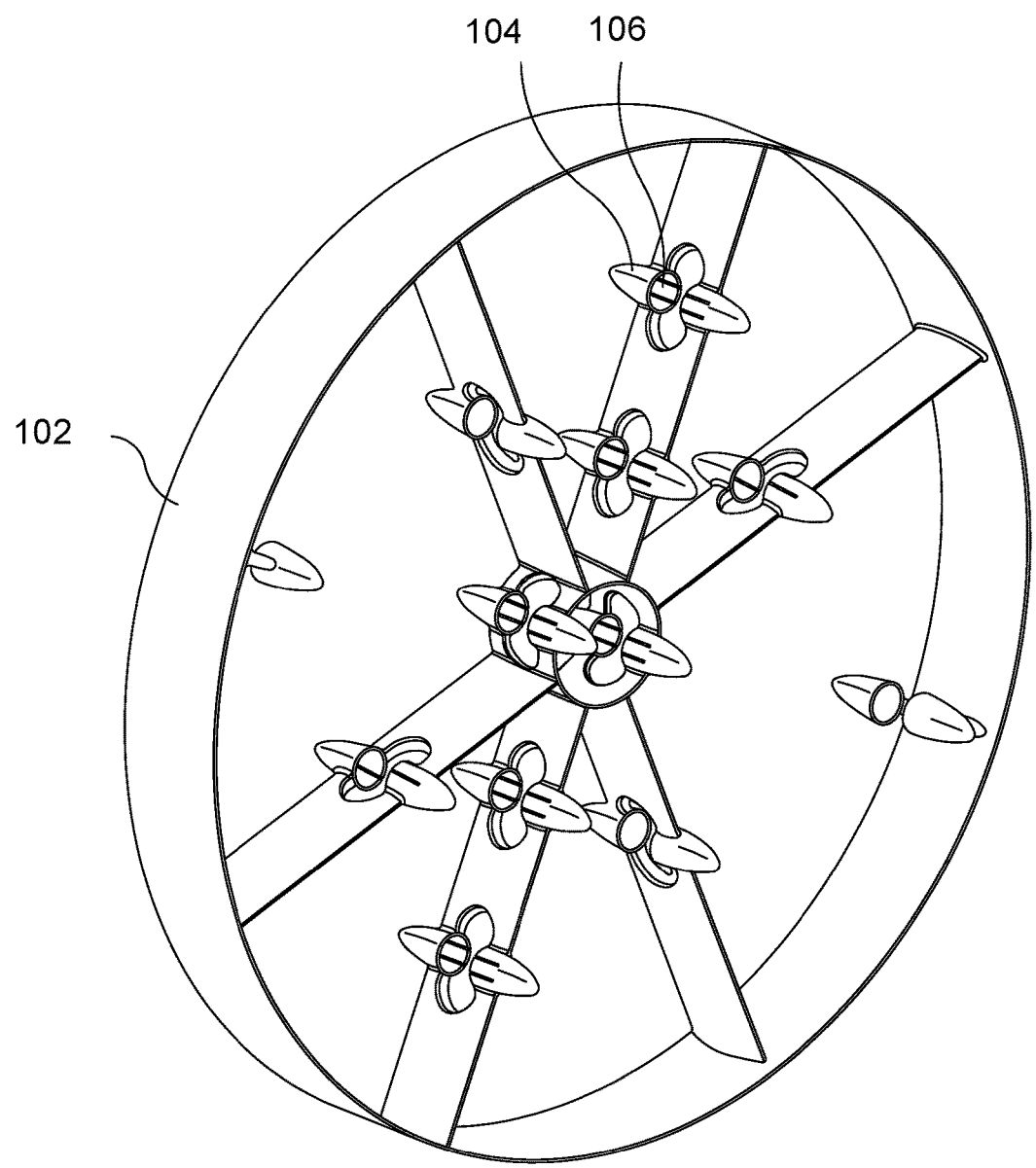
FIG. 1 illustrates a perspective view of an in-duct microphone support device in accordance with an embodiment of the present disclosure.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

Hereinafter, example embodiments will be described in more detail with reference to the accompanying drawings. The present invention, however, may be embodied in various different forms, and should not be construed as being limited to only the illustrated embodiments herein. Rather, these embodiments are provided as examples so that this disclosure will be thorough and complete, and will fully convey the aspects and features of the present invention to those skilled in the art. Accordingly, processes, elements, and techniques that are not necessary to those having ordinary skill in the art for a complete understanding of the aspects and features of the present invention may not be described. Unless otherwise noted, like reference numerals denote like elements throughout the attached drawings and the written description, and thus, descriptions thereof will not be repeated. In the drawings, the relative sizes of elements, layers, and regions may be exaggerated for clarity.

The present disclosure is directed to a method for measuring acoustic parameters in a duct over a relatively wider range of frequencies. An apparatus and a system for obtaining such acoustic measurements are also described.

Conventional techniques for measuring acoustic parameters (e.g., acoustic intensity) of acoustic waves (or sound waves) in a duct may include making a hole in a sidewall of the duct for mounting a microphone. The microphone may be mounted to the outside of the duct such that the microphone is flush against the interior sidewall of the duct. By mounting the microphone flush along the sidewall of the duct, acoustic intensity inside of the duct can be measured. However, such flush mounted microphone may be limited to measuring acoustics at one location. That is, the microphone mounted at one location along the sidewall of the duct is able to measure acoustic waves only at that one spot along the sidewall. This may not be concerning for acoustic frequencies that are below a cut-off frequency because acoustic waves below the cut-off frequency propagate mostly axially. However, when the frequency of the acoustic waves is higher than the cut-off frequency, the waves may propagate both tangentially and axially. Therefore, in order to more accurately measure the intensity of acoustic waves above the cut-off frequency, more microphones may be used to measure the intensity at various locations across the cross section of the duct. Moreover, conventional techniques for measuring the intensity typically require using high quality instrumentation grade microphones, which are generally relatively large in size and expensive. Thus, the size of the microphones may physically prevent a plurality of microphones from being mounted within the duct.

Furthermore, even if it is possible to place a plurality of large microphones in the duct, the microphones may take up too much space inside the duct and the microphones can affect the propagation of the waves. For example, if the microphones are too big, the waves may reflect off of the microphones and alter the direction of the propagation. Thus, an improved technique of implementing a plurality of smaller microphones (e.g., ¼ inch button microphones) across a cross sectional area of a duct without affecting the propagation path of the waves in the duct is needed to more accurately measure acoustic intensity, particularly above the cut-off frequency (e.g., 4-8 modes greater). While smaller microphones are typically less expensive, they are typically also lower in quality and are non-instrumentation grade microphones, which make them unsuitable for instrumentation based on the conventional techniques.

The present disclosure will describe techniques for using a plurality of microphones in a duct using smaller, inexpensive non-instrumentation grade microphones, while still achieving accurate acoustic measurements.

According to the embodiment, a plurality of small button size microphones are mounted on a low profile rack (or a microphone support device/structure used as a template), and the microphone support device is sized so that it may be placed in the duct to measure acoustic intensities within the duct. By placing a plurality of microphones across the cross sectional area of the duct, the microphones are able to measure sound intensity at multiple locations in the duct, thus more accurately measuring the intensity. That is, more acoustic intensity can be sampled within the duct, thus improving the overall measurement.

In some cases, small button size microphones may not be a high instrumentation grade microphone. That is, the microphones may be of a lower grade or quality, such as those used typically by a consumer, for example, on a cellular phone as opposed to a large high grade microphone that is used for instrumentation and testing. According to an embodiment of the present disclosure, lower grade microphones may be used by performing a calibration process on the microphones. Thus, by first calibrating the microphones, lower grade microphones may be mounted on the microphone structure in a predetermined arrangement to accurately measure the acoustic intensity in the duct.

FIG. 1 illustrates a perspective view of a circular microphone support device 102 having a shape that looks substantially like a wagon wheel. The microphone support device 102 has a circular outer perimeter structure and a circular inner structure with spoke-like structures (also referred to herein as "arms") between the outer and inner structures in a manner similar to that of a wagon wheel. The microphone support device 102 has microphone mounts 104 at predetermined locations along the outer perimeter structure, inner structure, and/or the arms, and each one of the microphone mounts 104 is configured to have a microphone 106 attached thereto. In some embodiments, the microphone mounts 104 are made such that the microphones 106 can be easily attached and/or removed by a user.

According to the embodiment, the outer perimeter structure, the inner structure, and the arms are designed to be as thin as possible while maintaining structural integrity in order to keep a low profile in the duct when installed. That is, when the microphone support device 102 is installed in the duct, it is designed to minimize interfering with and affecting the propagation properties of the acoustic wave so, as to obtain accurate measurements. Furthermore, in a case where there is air flowing through the duct in addition to the sound waves, the low profile of the structure minimizes affecting the air flow in the duct. For example, a larger or wider structure may disturb the flow of air in the duct, which in turn, can also affect the propagation of the acoustic waves within the duct.

In some embodiments, the microphones 106 are arranged as pairs of microphones. That is, for each microphone 106, there is a corresponding microphone at an opposite side of the structure, which forms the pair of microphones 106. The microphones 106 are paired with each other based on the phase characteristics of the microphones 106. The phase response of the microphones 106 can be determined through a phase calibration process which will be described in more detail later.

While various embodiments of the present disclosure describe the microphone support device 102 as having a circular wagon wheel shaped structure by way of example, the embodiments of the present disclosure are not limited thereto. Instead, the microphone support device 102 may come in other shapes and sizes based on the shape and size of the duct for which it is intended to be used with. For example, if a duct has a rectangular cross sectional shape, then the microphone support device 102 may also have a rectangular shape.

Figure 2A:
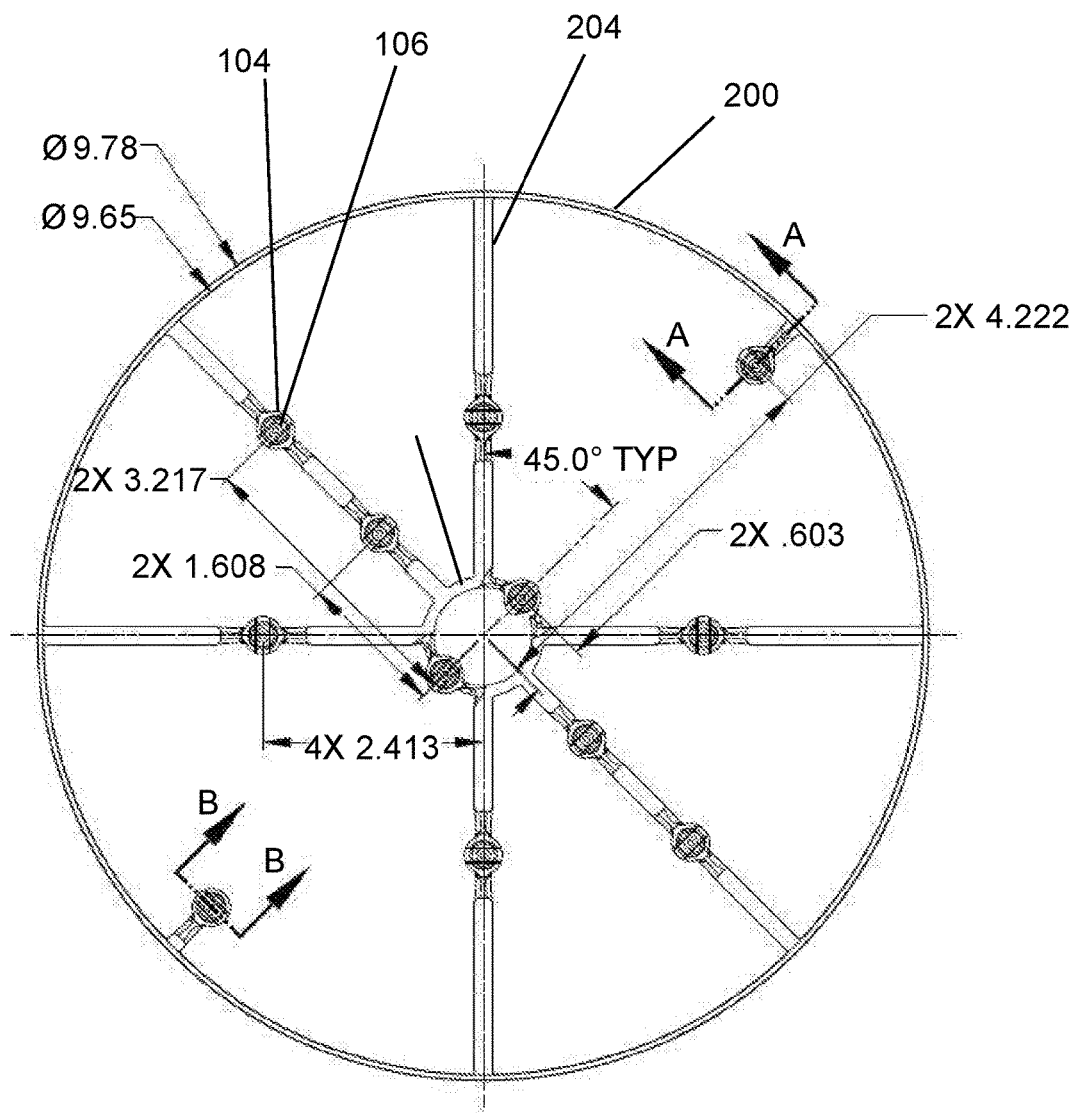
FIGS. 2A-2C illustrate an exemplary microphone support device in accordance with an embodiment of the present disclosure.
Figure 2B:
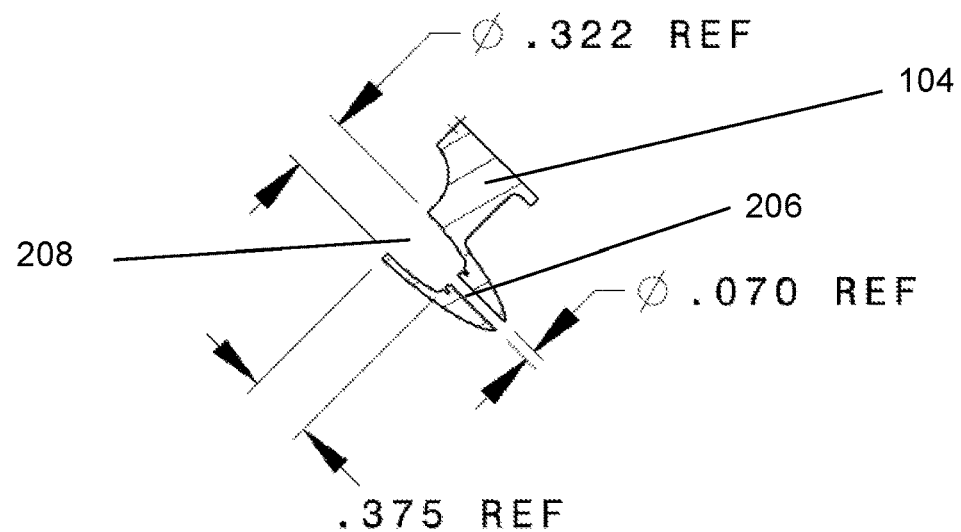
Figure 2C:
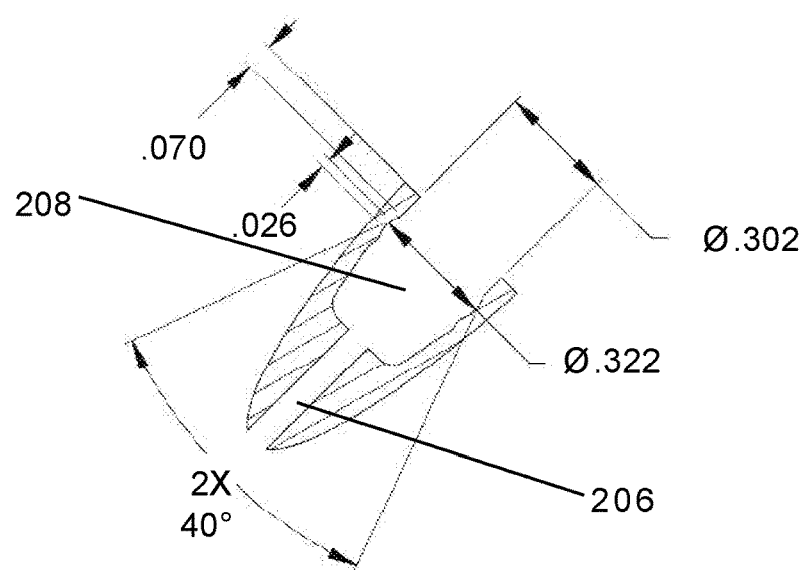

FIGS. 2A-2C illustrate an exemplary microphone support device according to an embodiment of the present disclosure. The microphone support device illustrated in FIG. 2A is similar to the embodiment illustrated in FIG. 1. According to the embodiment, the microphone support device 102 includes an outer circular structure 200, an inner circular structure 202, and arms 204 extending between the outer circular structure 200 and the inner circular structure 202. According to this embodiment, there are six arms 204 with each arm including one or more microphone mounts 104 with microphones 106. Additionally, there are two additional microphone mounts 104 coupled to the outer circular structure 200, each one with a microphone 106 attached thereto.

As such, the microphone support device 102 shown in FIG. 2A includes microphone mounts 104 positioned at various predetermined locations on the structures of the microphone support device 102.

Figure 3:
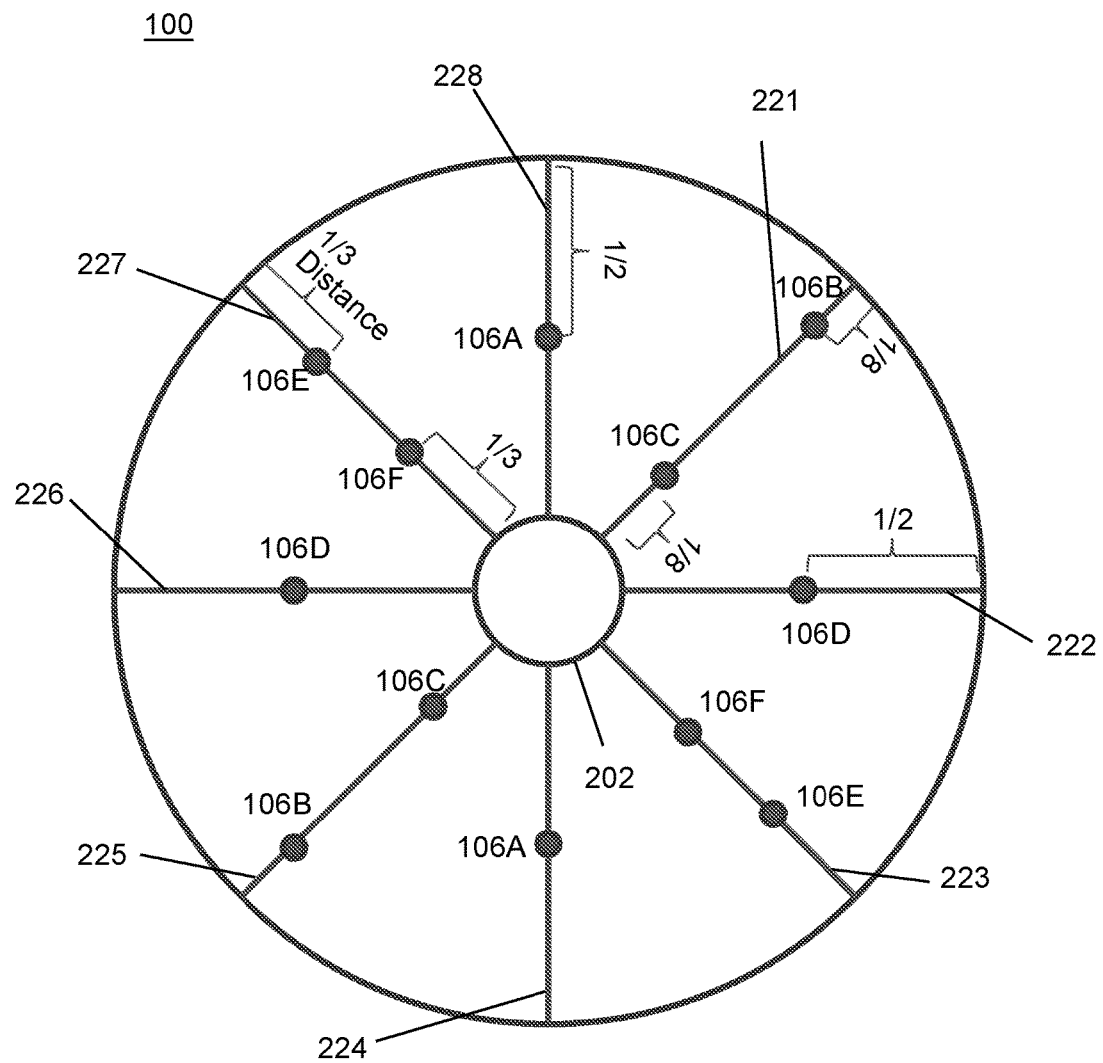
FIG. 3 illustrates an exemplary arrangement of microphones on a microphone support device in accordance with an embodiment of the present disclosure.

In some embodiments, the specific location of the microphone mounts 104 and the microphones 106 are determined based on a fractional radius of the microphone support device 102. FIG. 3 illustrates an example arrangement of a plurality of microphones 106 on the microphone support device 102. For example, one microphone mount 104 may be located on one of the arms 204 at a distance of ½ the radius of the outer circular structure 200. More specifically, according to this example arrangement, the distance between microphones 106A and 106D and the outer circular structure 200 is about ½ the radius of the outer circular structure 200. The distance between microphones 106B and the outer circular structure 200 is about ⅛ the radius of the outer circular structure 200. The distance between microphones 106C and the center of the circular structure is about ⅛ the radius of the outer circular structure 200. The distance between microphones 106E and the outer circular structure 200 is about ⅓ the radius of the outer circular structure 200. The distance between microphones 106F and the center of the circular structure is about ⅓ the radius of the outer circular structure 200. Because the locations of the microphones 106 are determined based on fractional radius of the microphone support device 102, the predetermined arrangement may be scaled to accommodate microphone support devices of various sizes. As such, the amount and the locations of the microphones 106 may be arranged in a manner so as to distribute them across the cross sectional area of the duct to obtain an accurate sample of the acoustic waves propagating down the duct. Placing too many microphones in the duct may affect the propagation of the waves by blocking or redirecting the acoustic waves, while having an insufficient amount of microphones 106 in the duct may make it difficult to obtain a representative sample of the acoustic waves propagating in the duct. Furthermore, the fractional distances specified with reference to FIG. 3 is merely by way of example and not intended to be limiting. Therefore, more or fewer number of microphones 106 may be included and the microphones 106 may be arranged according to other fractional distances or dimensions.

In the present disclosure, reference numeral 106 is intended to refer to any of the one or more microphones according to the various embodiments. Reference numeral 106 followed by an alphabet (e.g., 106A) refers to a specific microphone. Furthermore, the alphabet indicates that the two microphones are pairs with one another.

In some embodiments, the outer circular structure 200 is sized to be smaller than the inner diameter of the duct so that it can snuggly fit inside of the duct. In some embodiments, the microphone support device 102 is a portable device that is temporarily placed in the duct to measure acoustic intensities and is then removed when the measurements are obtained.

FIG. 2B illustrates a cross sectional view of microphone mount 104 along the lines A-A of FIG. 2A. FIG. 2C illustrates a cross sectional view of microphone mount 104 along the lines B-B of FIG. 2A. According to an embodiment, microphone 106 is adapted to fit in cavity 208 in microphone mount 104. Microphone mount 104 has an opening 206 for passing microphone wires through. In some embodiments, the microphone wires from all of the microphones 106 on the microphone support device 102 may be bundled together and routed to an external system such as a computer.

Figure 4A:
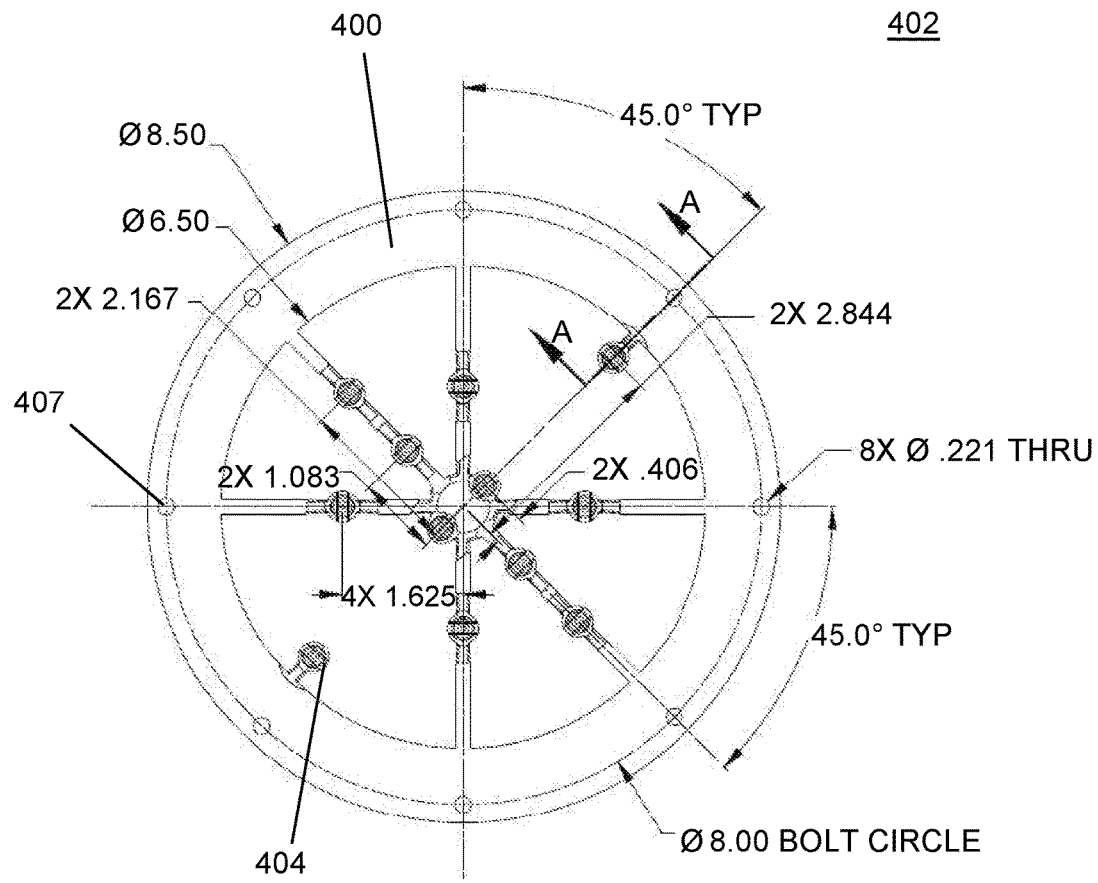
FIGS. 4A-4B illustrate an exemplary microphone support device in accordance with another embodiment of the present disclosure.
Figure 4B:
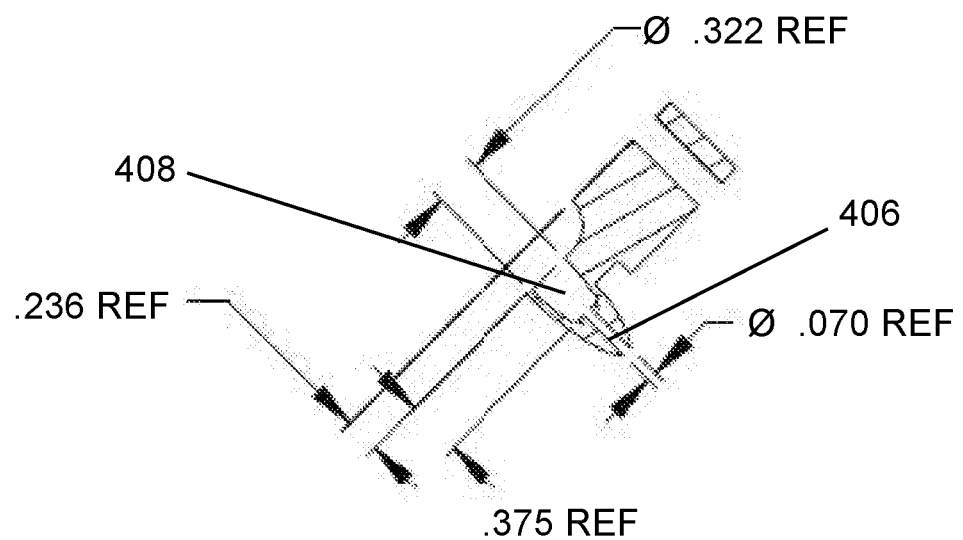

FIGS. 4A-4B illustrate a microphone support device 402 according to another embodiment of the present disclosure. In this embodiment, the outer circular structure 400 of the microphone support device 402 is larger than the outer circular structure 200 illustrated in the embodiment of FIG. 2A. The microphone support device 402 according to this embodiment may be mounted, for example, to an end of the duct with screws 407. Thus, the outer circular structure 400 has sufficient space to apply screws to mount to the duct. The plurality of microphones are distributed in a manner similar to that described with reference to FIG. 2A.

FIG. 4B is a cross sectional view of a microphone mount 406 along the lines A-A of FIG. 4A. Similar to the microphone mount 104 illustrated in FIG. 2B-2C, the microphone mount 404 includes a cavity 408 where a microphone 106 may be attached. In some embodiments, the microphone mount 404 has an opening 406 for passing microphone wires through.

Figure 5C:
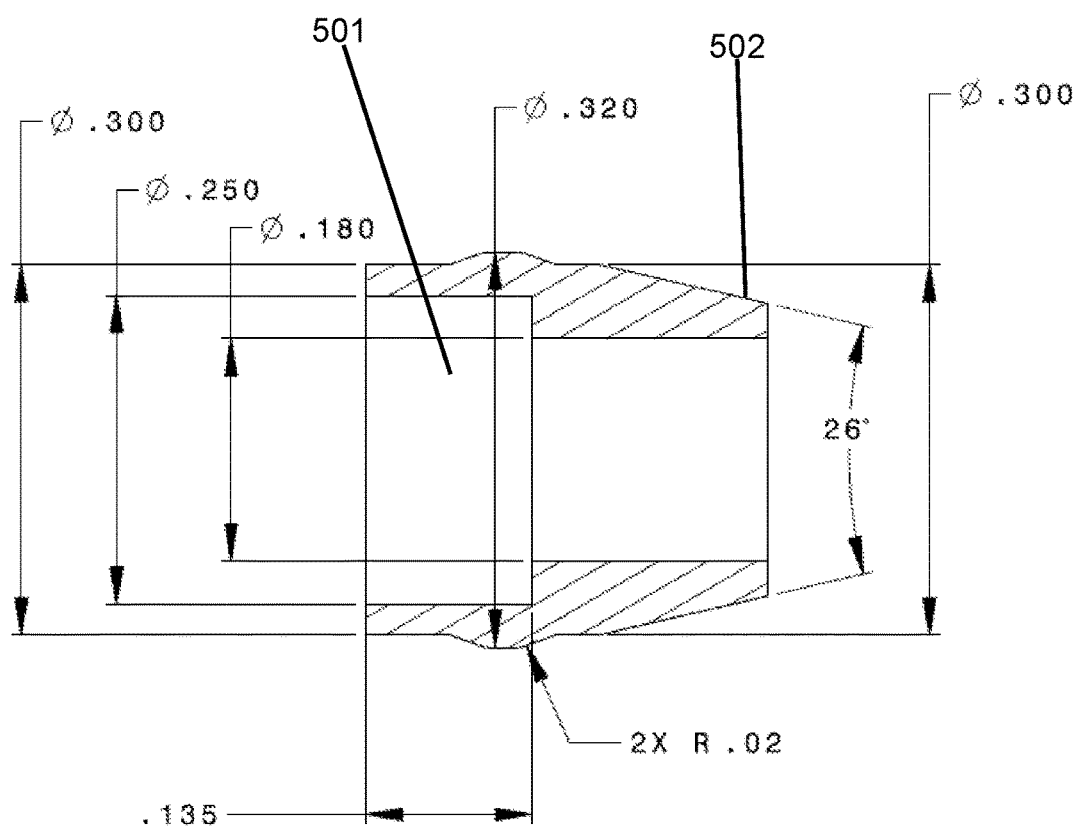

FIGS. 5A-5C illustrate various views of a microphone holder. In some embodiments, small button size microphones may be used to measure acoustic waves according to the techniques of the present disclosure. Microphone holder 500 illustrated in FIGS. 5A-5C may be used to hold the button size microphones in place, and in turn, the microphone holder 500 may be coupled to microphone mount 104 illustrated in FIGS. 2 and 4. More specifically, the microphone holder 500 is adapted to hold the button size microphone in slot 501 (in FIG. 5C) and end portion 502 is adapted to snuggly fit into slot 208 of FIG. 2B or slot 408 of FIG. 4B. The microphone holder 500 illustrated in FIGS. 5A-5C is not intended to be limiting, but is instead intended to be an exemplary technique for mounting the microphones to the microphone support device.

Figure 6:
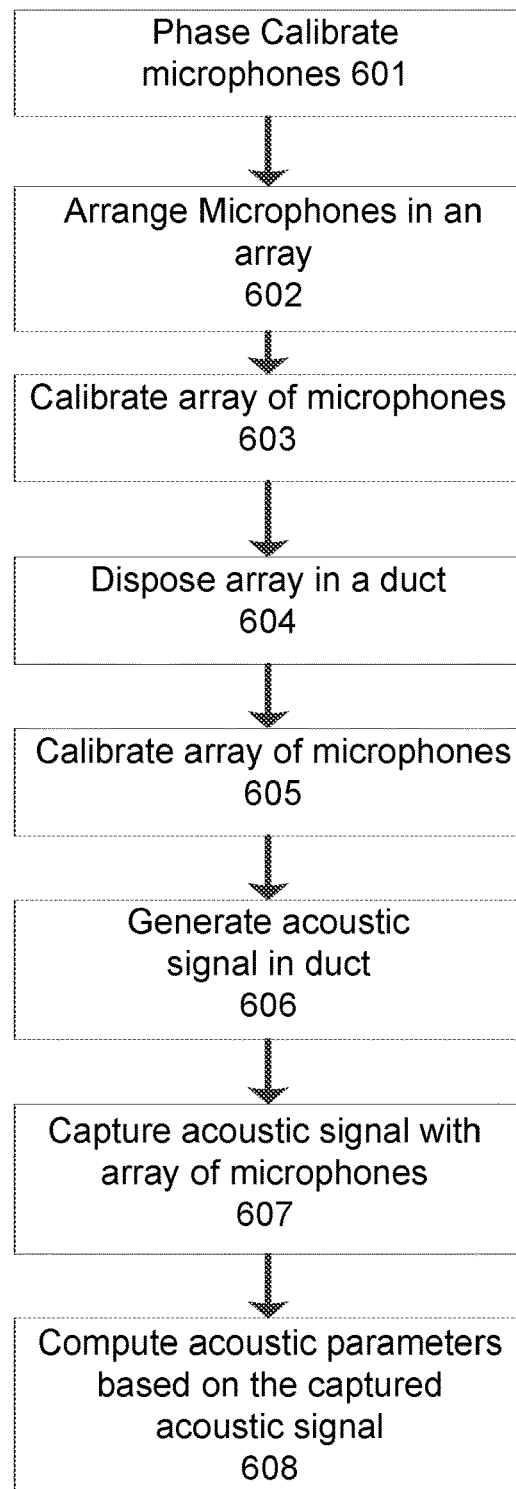
FIG. 6 is a flow chart of an exemplary method for measuring acoustic parameters in a duct in accordance with an embodiment of the present disclosure.

FIG. 6 is a flow chart of an exemplary method for measuring acoustic parameters in a duct. According to an embodiment of the present disclosure, at block 601, a plurality of microphones are phase calibrated. During phase calibration, each microphone is placed into a phase calibration device that accommodates a microphone that is to be phase calibrated and a reference microphone having a known phase response. The phase calibration device is coupled to a speaker and the speaker is configured to output a flat acoustic signal of white noise. Data based on the phase response of the microphone is then collected from the calibration device and loaded into a computer program such as, for example MATLAB®, to plot the phase response of all of the microphones. Once the phase response is determined for each microphone, two microphones having a phase response that are most similar to one other are assigned to be a pair of microphones. As such, phase calibration of the microphones allow for using lower quality, non-instrumentation grade microphones to measure acoustic intensities.

Next at block 602, the plurality of microphones are arranged on the microphone support device according to the techniques described in various embodiments of the present disclosure. Once the microphones are arranged on the microphone support device, at block 603, a sound pressure level calibration is performed to calibrate a conversion factor between the voltage levels read by the microphone to pressure levels provided to the user. Once the microphones are sound pressure level calibrated, at block 604, the microphone support device may be placed in the duct, or alternatively, mounted to the duct using screws or clips. After the microphone support device is placed in the duct, another sound pressure level calibration is performed again to ensure no degradation of the microphone occurred at block 605. At block 606, an acoustic signal generator or a noise generator may be positioned in the duct to generate known acoustic waves. In some embodiments, noise from machinery may be used, for example, by turning on equipment such as an air conditioning system located upstream in the duct. Yet in some embodiments, ambient noise generated by air flow in the duct may be used. At block 607, the array of microphones captures the acoustic waves in the duct to provide acoustic parameter data to a computer. At block 608, the computer may compute the acoustic parameter data to generate values for the acoustic intensity of the wave measured by the array of microphones.

Figure 7:
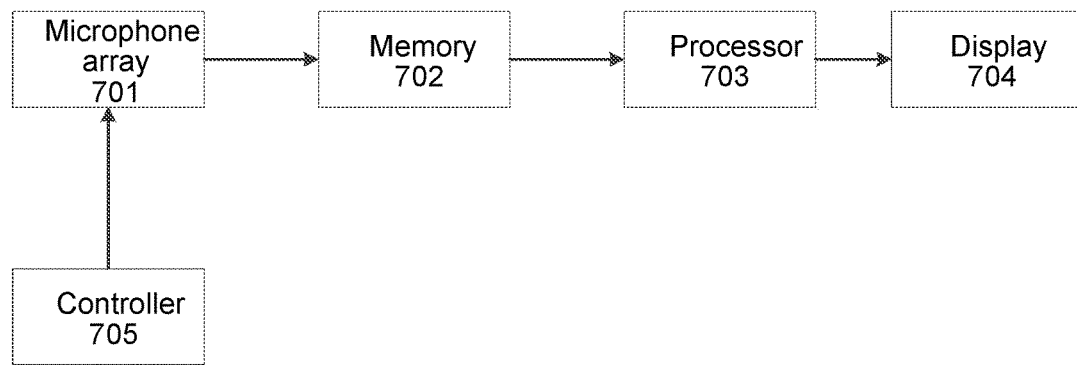
FIG. 7 is a block diagram of an in-duct acoustic measuring system in accordance with an embodiment of the present disclosure.

FIG. 7 is a block diagram of a system 700 for measuring acoustic parameters in a duct. According to an embodiment of the present disclosure, an array a microphones is positioned on a microphone support device according to a predetermined arrangement. The array of microphones may be configured to measure the acoustic intensity in the duct in response to a signal provided by a controller 705. The measured acoustic intensity is then provided to a computer that includes a memory 702 and a processor 703. The processor 703 may be configured to execute instructions stored in the memory 702 in order to process and analyze the acoustic parameter data obtained by the microphones. Furthermore, the memory 702 may store acoustic parameter data for retrieval by the user in the future, for example, to perform trend analysis of the acoustic parameters.

It will be understood that, although the terms "first," "second," "third," etc., may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present invention.

Spatially relative terms, such as "beneath," "below," "lower," "under," "above," "upper," and the like, may be used herein for ease of explanation to describe one element or feature's relationship to another element(s) or feature(s) as illustrated in the figures. It will be understood that the spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented (e.g., rotated 90 degrees or at other orientations) and the spatially relative descriptors used herein should be interpreted accordingly.

It will be understood that when an element or layer is referred to as being "on," "connected to," or "coupled to" another element or layer, it can be directly on, connected to, or coupled to the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

The terminology used herein is for the purpose of describing particular embodiments and is not intended to be limiting of the present invention. As used herein, the singular forms "a" and "an" are intended to include the plural forms as well, unless the context clearly indicates otherwise. It will be further understood that the terms "comprises," "comprising," "includes," and "including," when used in this specification, specify the presence of the stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list.

As used herein, the terms "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present invention refers to "one or more embodiments of the present invention." As used herein, the terms "use," "using," and "used" may be considered synonymous with the terms "utilize," "utilizing," and "utilized," respectively. Also, the term "exemplary" is intended to refer to an example or illustration.

The electronic or electric devices and/or any other relevant devices or components according to embodiments of the present invention described herein may be implemented utilizing any suitable hardware, firmware (e.g. an application-specific integrated circuit), software, or a combination of software, firmware, and/or hardware. For example, the various components of these devices may be formed on one integrated circuit (IC) chip or on separate IC chips. Further, the various components of these devices may be implemented on a flexible printed circuit film, a tape carrier package (TCP), a printed circuit board (PCB), or formed on one substrate. Further, the various components of these devices may be a process or thread, running on one or more processors, in one or more computing devices, executing computer program instructions and interacting with other system components for performing the various functionalities described herein. The computer program instructions are stored in a memory which may be implemented in a computing device using a standard memory device, such as, for example, a random access memory (RAM). The computer program instructions may also be stored in other non-transitory computer readable media such as, for example, a CD-ROM, flash drive, or the like. Also, a person of skill in the art should recognize that the functionality of various computing devices may be combined or integrated into a single computing device, or the functionality of a particular computing device may be distributed across one or more other computing devices without departing from the spirit and scope of the exemplary embodiments of the present invention.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and/or the present specification, and should not be interpreted in an idealized or overly formal sense, unless expressly so defined herein.

Embodiments described herein are exemplary only. One skilled in the art may recognize various alternative embodiments from those specifically disclosed. Those alternative embodiments are also intended to be within the scope of this disclosure. As such, the embodiments are limited only by the following claims and their equivalents.

The invention claimed is:

1. A method for measuring one or more acoustic parameters comprising at least an acoustic intensity in a duct, the method comprising:
   arranging at least one pair of microphones in an array on a microphone support device, wherein the microphone support device is configured to fit within an inner diameter of the duct and extend across a cross-section of the duct;
   disposing the microphone support device comprising the array of microphones in the duct;
   generating an acoustic signal within a volume of the duct such that the acoustic signal propagates within the volume of the duct in an axial direction down the duct toward the array of microphones; and
   receiving by the at least one pair of microphones in the array of microphones, the acoustic signal to measure the acoustic intensity of the acoustic signal propagating within the volume of the duct and to provide a microphone output signal.

2. The method of claim 1, further comprising phase calibrating a plurality of microphones, and in response to the phase calibration, selecting at least one pair of microphones based on a phase response of the microphones.

3. The method of claim 2, wherein the phase calibrating comprises:
   determining the phase response for each microphone of the plurality of microphones; and
   pairing a first microphone with a second microphone having the phase response matching the phase response of the first microphone.

4. The method of claim 1, wherein the one or more acoustic parameters further comprise an acoustic frequency, and/or an acoustic pressure, and wherein the acoustic intensity, the acoustic frequency and/or the acoustic pressure are associated with the acoustic signal being generated by an air flow, an acoustic signal generator, or a noise generator.

5. The method of claim 4, further comprising processing the microphone output signal by a processor to compute the intensity of the acoustic signal.

6. The method of claim 1, wherein the array of microphones is arranged in a wagon wheel configuration comprising spokes, each microphone of the array of microphones being disposed along the spokes of the wagon wheel configuration, and wherein the duct is a substantially cylindrical shape.

7. The method of claim 6, wherein the array of microphones is in multiples of two microphones.

8. The method of claim 1, wherein the duct is a substantially rectangular shape.

9. A method for arranging microphones in a duct for measuring one or more acoustic parameters comprising at least an acoustic intensity within the duct, the method comprising:
   providing a microphone support device, wherein the microphone support device is configured to fit within an inner diameter of the duct and extend across a cross-section of the duct;
   mounting at least one pair of microphones at predetermined locations along the microphone support device; and
   receiving, by the at least one pair of microphones mounted along the microphone support device, an acoustic signal that propagates within a volume the duct in an axial direction down the duct toward the microphones to measure the acoustic intensity of the acoustic signal propagating within the volume of the duct.

10. The method of claim 9, wherein the microphones are arranged as an array, wherein the one or more acoustic parameters further comprise an acoustic frequency, and/or an acoustic pressure, and wherein the acoustic intensity, the acoustic frequency, and/or the acoustic pressure are associated with the acoustic signal being generated by an air flow, an acoustic signal generator, or a noise generator.

11. The method of claim 9, wherein the predetermined locations are based on a fractional radius of the microphone support device.

12. The method of claim 10, wherein the array of microphones are arranged in a wagon wheel configuration having spokes, each microphone of the array of microphones being disposed along the spokes of the wagon wheel configuration, and wherein the duct is a substantially cylindrical shape.

13. The method of claim 10 wherein the duct is a substantially rectangular shape.

14. The method of claim 10, wherein the microphone support device comprises cavities and the microphones are mounted in the cavities.

15. An apparatus comprising the microphone support device arranged according to the method of claim 9 and configured to measure one or more acoustic parameters in the duct.

16. An apparatus comprising:
   a microphone support device configured to fit within an inner diameter of a duct and extend across a cross-section of the duct; and
   a plurality of microphones arranged in an array on the microphone support device, each of the plurality of microphones being disposed at predetermined locations along the microphone support device configured to receive an acoustic signal that propagates within a volume the duct in an axial direction down the duct toward the array of microphones to measure an acoustic intensity of the acoustic signal propagating within the volume of the duct.

17. The apparatus of claim 16, wherein the array of microphones are arranged in a wagon wheel configuration, and wherein the duct is a substantially cylindrical shape.

18. The apparatus of claim 17, wherein the microphone support device is configured to be removable from the duct.

19. A method for phase calibrating the array of microphones of claim 1, the method comprising:
   determining a phase response for each of the microphones; and
   pairing a first microphone of the array of microphones with a second microphone of the array of microphones, wherein the phase response of the first microphone matches the phase response of the second microphone.

20. The method of claim 19, wherein the determining of the phase response comprises:
   obtaining phase data by applying a white noise signal to each microphone; and
   plotting the phase data on a computer system to visually compare the phases.

* * * * *

UNITED STATES PATENT AND TRADEMARK OFFICE
CERTIFICATE OF CORRECTION

PATENT NO. : 10,337,757 B2
APPLICATION NO. : 15/253787
DATED : July 2, 2019
INVENTOR(S) : Remy M. Gutierrez, Bernard J. Sklanka and Ian M. Gunter Page 1 of 1

It is certified that error appears in the above-identified patent and that said Letters Patent is hereby corrected as shown below:

In the Claims

In Column 10, Line 1, change "volume the" to --volume of the--.
In Column 10, Line 41, change "volume the" to --volume of the--.

Signed and Sealed this
Twenty-eighth Day of April, 2020

Andrei Iancu
*Director of the United States Patent and Trademark Office*